US009119970B2

(12) United States Patent
Van Funderburk

(10) Patent No.: US 9,119,970 B2
(45) Date of Patent: Sep. 1, 2015

(54) FEEDTHROUGH ASSEMBLY WITH GLASS LAYER AND ELECTRICAL STIMULATION SYSTEMS CONTAINING THE ASSEMBLY

(71) Applicant: BOSTON SCIENTIFIC NEUROMODULATION CORPORATION, Valencia, CA (US)

(72) Inventor: Jeffery Van Funderburk, Stevenson Ranch, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/457,674

(22) Filed: Aug. 12, 2014

(65) Prior Publication Data

US 2015/0051676 A1 Feb. 19, 2015

Related U.S. Application Data

(60) Provisional application No. 61/867,416, filed on Aug. 19, 2013.

(51) Int. Cl.
*A61N 1/375* (2006.01)
*B23K 1/00* (2006.01)
*B23K 1/19* (2006.01)
*C03C 27/08* (2006.01)

(52) U.S. Cl.
CPC ............ *A61N 1/3754* (2013.01); *B23K 1/0008* (2013.01); *B23K 1/19* (2013.01); *C03C 27/08* (2013.01)

(58) Field of Classification Search
None
See application file for complete search history.

(56) References Cited

U.S. PATENT DOCUMENTS

| 4,991,582 A | * | 2/1991 | Byers et al. ................. 607/2 |
| 5,246,000 A | | 9/1993 | Ellis et al. |
| 5,514,162 A | | 5/1996 | Bornzin et al. |
| 5,866,851 A | * | 2/1999 | Taylor et al. .......... 174/152 GM |

(Continued)

FOREIGN PATENT DOCUMENTS

WO 2011051094 A1 5/2011

OTHER PUBLICATIONS

Park et al., Calculation of MRI-Induced Heating of an Implanted Medical Lead Wire With an Electric Field Transfer Function: Journal of Magnetic Resonance Imaging 26:1278-1285 (2007).

(Continued)

*Primary Examiner* — Kennedy Schaetzle
(74) *Attorney, Agent, or Firm* — Lowe Graham Jones PLLC; Bruce E. Black

(57) ABSTRACT

A control module for an electrical stimulation system includes a casing defining a sealed inner compartment; an electronic subassembly disposed in the inner compartment; and a header portion coupled to the casing and having a connector to receive a proximal end of a lead or lead extension. The connector includes conductive contacts to electrically couple to terminal contacts on the lead or lead extension. The control module also includes a feedthrough assembly coupling the casing to the header portion. The feedthrough assembly includes a non-conductive ceramic block coupled to the casing, conductive feedthrough pins passing through the ceramic block and electrically coupling the conductive contacts of the connector to the electronic subassembly, a metal braze coupling the feedthrough pins to the ceramic block, and at least one glass layer disposed on at least a portion of the ceramic block and in contact with at least one of the feedthrough pins.

20 Claims, 6 Drawing Sheets

(56) References Cited

U.S. PATENT DOCUMENTS

| | | | |
|---|---|---|---|
| 6,181,969 B1 | 1/2001 | Gord | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 6,932,644 B1 * | 8/2005 | Taylor | 439/566 |
| 7,170,297 B1 | 1/2007 | Dunsmore | |
| 7,244,150 B1 | 7/2007 | Brase et al. | |
| 7,437,193 B2 | 10/2008 | Parramon et al. | |
| 7,672,734 B2 | 3/2010 | Anderson et al. | |
| 7,761,165 B1 | 7/2010 | He et al. | |
| 7,949,395 B2 | 5/2011 | Kuzma | |
| 7,974,706 B2 | 7/2011 | Moffitt et al. | |
| 8,175,710 B2 | 5/2012 | He | |
| 8,224,450 B2 | 7/2012 | Brase | |
| 8,364,278 B2 | 1/2013 | Pianca et al. | |
| 8,675,338 B2 * | 3/2014 | Teske | 361/302 |
| 2006/0009813 A1 * | 1/2006 | Taylor et al. | 607/36 |
| 2006/0247714 A1 * | 11/2006 | Taylor et al. | 607/36 |
| 2007/0150036 A1 | 6/2007 | Anderson | |
| 2008/0243218 A1 | 10/2008 | Bottomley et al. | |
| 2009/0292326 A1 * | 11/2009 | Fang et al. | 607/2 |
| 2011/0160808 A1 | 6/2011 | Lyden et al. | |
| 2014/0345934 A1 * | 11/2014 | Markham et al. | 174/667 |
| 2015/0051676 A1 * | 2/2015 | Van Funderburk | 607/116 |

OTHER PUBLICATIONS http://www.osti.gov/energycitations/product.biblio.jsp?osti_id=5252319; Energy Citations Database (ECD), Document #5252319, 2 pages, Jun. 20, 2013.

* cited by examiner

FEEDTHROUGH ASSEMBLY WITH GLASS LAYER AND ELECTRICAL STIMULATION SYSTEMS CONTAINING THE ASSEMBLY

CROSS-REFERENCE TO RELATED APPLICATIONS

This application claims the benefit under 35 U.S.C. §119 (e) of U.S. Provisional Patent Application Ser. No. 61/867,416, filed Aug. 19, 2013, which is incorporated herein by reference.

FIELD

The present invention is directed to the area of implantable electrical stimulation systems and methods of making and using the systems. The present invention is also directed towards feedthrough assemblies that include both a glass layer and a metal braze and implantable electrical stimulation systems containing the feedthrough assemblies as well as methods of making and using the feedthrough assembly and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a control module for an electrical stimulation system. The control module includes a casing defining a sealed inner compartment; an electronic subassembly disposed in the inner compartment of the casing; and a header portion coupled to the casing and having a connector to receive a proximal end of at least one lead or lead extension. The connector includes conductive contacts to electrically couple to terminal contacts on the at least one lead or lead extension. The control module also includes a feedthrough assembly coupling the casing to the header portion and, in combination with the casing, sealing the inner compartment of the casing. The feedthrough assembly includes a non-conductive ceramic block coupled to the casing, conductive feedthrough pins passing through the ceramic block and electrically coupling the conductive contacts of the connector to the electronic subassembly disposed in the inner compartment of the casing, a metal braze coupling the feedthrough pins to the ceramic block, and a glass layer disposed on at least a portion of the ceramic block and in contact with at least one of the feedthrough pins.

Another embodiment is a control module for an electrical stimulation system. The control module includes a casing defining a sealed inner compartment and having a metal portion; an electronic subassembly disposed in the inner compartment of the casing; and a header portion coupled to the casing and having a connector to receive a proximal end of at least one lead or lead extension. The connector includes conductive contacts to electrically couple to terminal contacts on the at least one lead or lead extension. The control module also includes a feedthrough assembly between the casing and the header portion and, in combination with the casing, sealing the inner compartment of the casing. The feedthrough assembly includes a non-conductive ceramic block coupled to the metal portion of the casing, conductive feedthrough pins passing through the ceramic block and electrically coupling the conductive contacts of the connector to the electronic subassembly disposed in the inner compartment of the casing, a metal braze coupling the feedthrough pins to the ceramic block, and a glass layer disposed on at least a portion of the ceramic block and in contact with each of the feedthrough pins to form a hermetic seal around the feedthrough pins.

Yet another embodiment is a method of forming a feedthrough assembly for a control module of an implantable electrical stimulation system. The method includes disposing feedthrough pins through openings in a ceramic block; attaching the feedthrough pins to the ceramic block using a metal braze; and, after attaching the feedthrough pins, forming a glass layer on at least a portion of the ceramic block and in contact with each of the feedthrough pins.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed towards feedthrough assemblies that include both a glass layer and a metal braze and implantable electrical stimulation systems containing the feedthrough assemblies as well as methods of making and using the feedthrough assembly and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
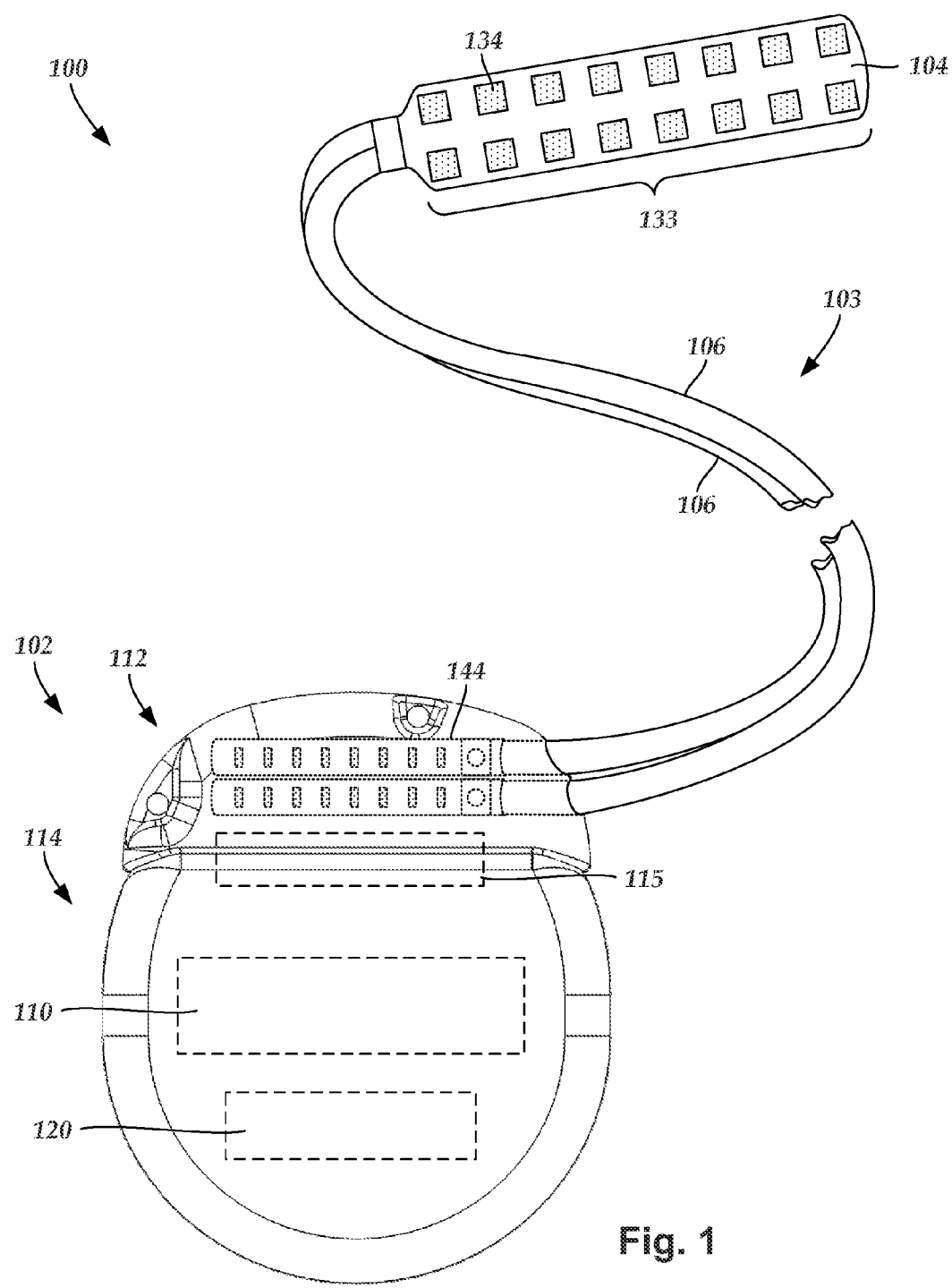
FIG. 1 is a schematic side view of an embodiment of an electrical stimulation system that includes a paddle lead electrically coupled to a control module, according to the invention.

FIG. 1 illustrates schematically an embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array of electrodes 133, such as electrode 134, is disposed on the paddle body 104, and an array of terminals (e.g., 310 in FIG. 3) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
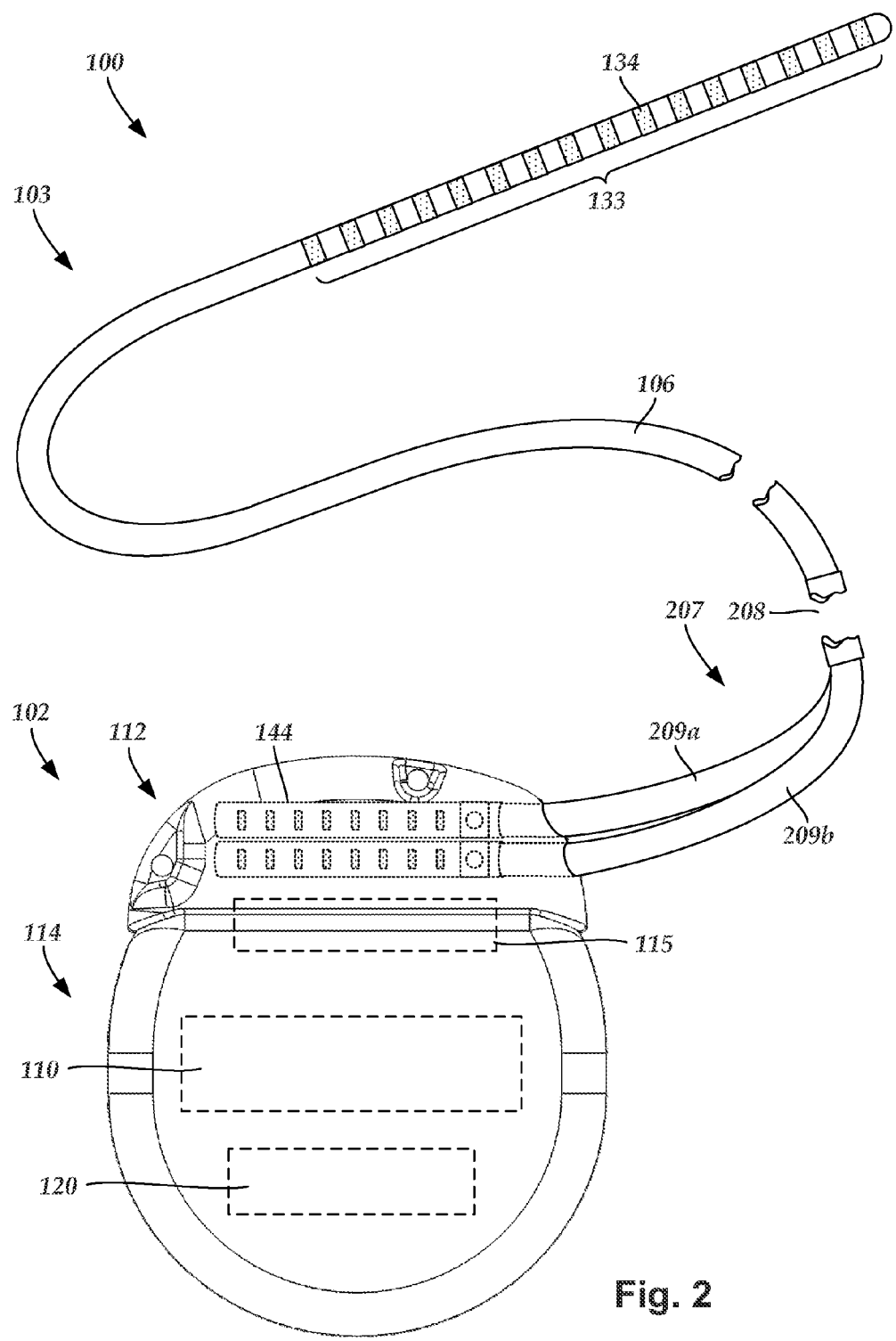
FIG. 2 is a schematic side view of an embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (300 in FIGS. 3A-3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 207 configured and arranged for facilitating coupling of the lead 103 to the control module 102. The splitter 207 includes a splitter connector 208 configured to couple to a proximal end of the lead 103, and one or more splitter tails 209a and 209b configured and arranged to couple to the control module 102 (or another splitter, a lead extension, an adaptor, or the like).

The control module 102 typically includes a header portion 112 and a sealed casing 114. The casing 114 may be formed, at least in part, of metal or have a metal coating disposed on at least a portion of the casing. An electronic subassembly 110 and an optional power source 120 are disposed in a sealed compartment within the casing 114. A control module connector 144 is disposed in the header portion 112. The control module connector 144 is configured and arranged to make an electrical connection between the lead 103 and the electronic subassembly 110 of the control module 102. The control module also includes a feedthrough assembly 115 for electrically coupling the connector 144 of the header portion 112 to the internal electronic subassembly 110 in the casing 114

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 and may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
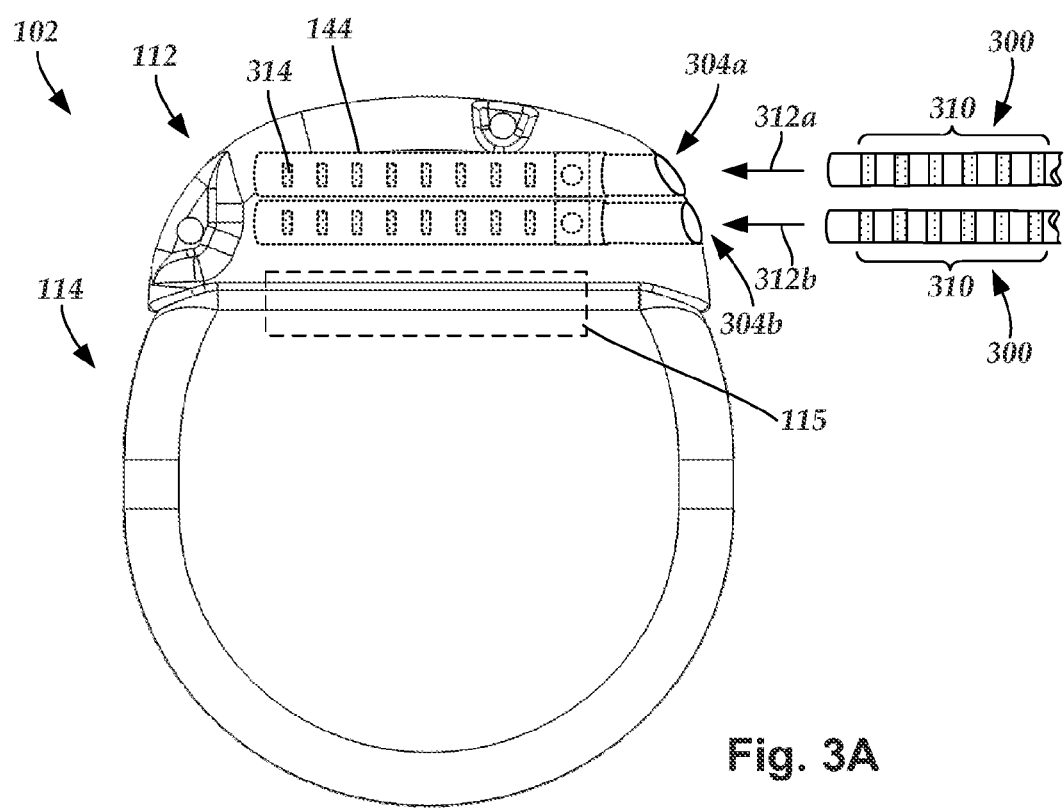
FIG. 3A is a schematic side view of an embodiment of the control module of FIG. 1 configured and arranged to electrically couple to an elongated device, according to the invention.
Figure 3B:
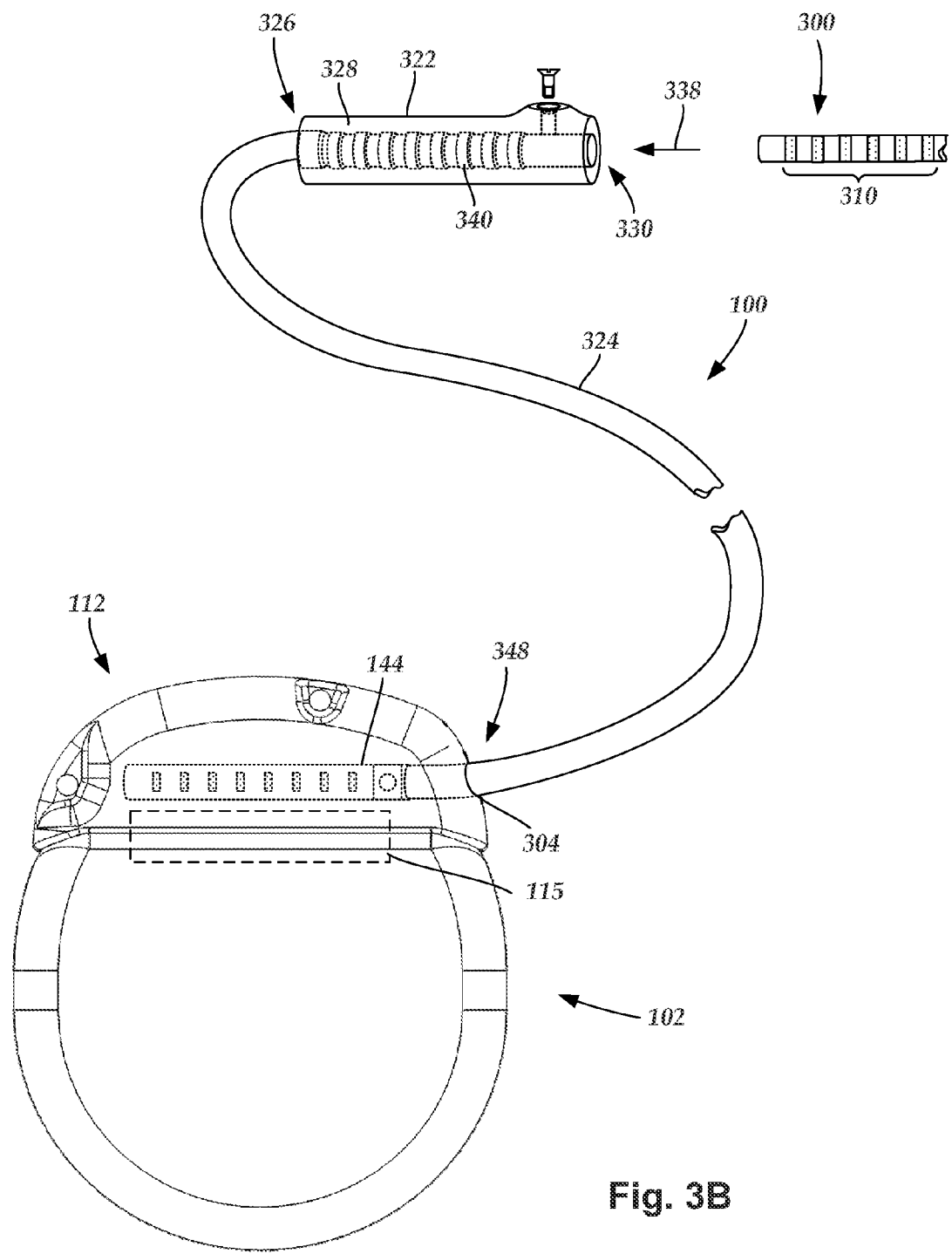
FIG. 3B is a schematic side view of an embodiment of a lead extension configured and arranged to electrically couple the elongated device of FIG. 2A to the control module of FIG. 1.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIGS. 3A-3B). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors may extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may also be one or more lumens (not shown) that open at, or near, the distal end of the one or more lead bodies 106, for example, for infusion of drugs or medication into the site of implantation of the one or more lead bodies 106. In at least one embodiment, the one or more lumens may be flushed continually, or on a regular basis, with saline, epidural fluid, or the like. In at least some embodiments, the one or more lumens can be permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the header portion 112 is shown having two ports 304a and 304b. The header portion 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 207 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 200, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contact 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144. The header portion 112 housing the control module connector 144 may not be hermetically sealed as the lead(s) 106 are inserted into the port(s) 304 of the header portion 112.

Figure 4:
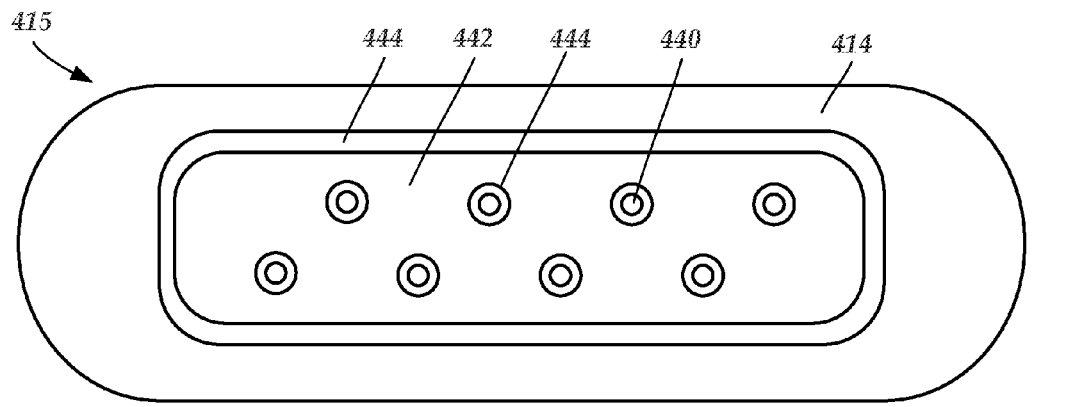
FIG. 4 is a schematic bottom view of one embodiment of a feedthrough assembly and a portion of a casing of a control module, according to the invention.

FIG. 4 illustrates a bottom view (i.e., the side facing the sealed compartment of the casing) of one embodiment of a feedthrough assembly 415 and a portion of a casing of 414 of a control module (102 as shown in FIG. 3B). The feedthrough assembly 415 includes a ceramic block 442 with a number of feedthrough pins 440 passing through the ceramic block 442 to electrically couple to the electronic subassembly (110 as shown in FIG. 2) encased within the casing 414. A metal braze 444 is disposed around the periphery of the ceramic block 442 and each of the pins 440 to attach the casing 414 and the pins 440 to the ceramic block 442. The attachment provided by the metal braze 644 is preferably forms a hermetic seal, but, as described below, the seal can be provided or enhanced using a layer of glass.

The feedthrough pins 440 are positioned on the ceramic block 442 in any suitable arrangement. For example, the feedthrough pins 440 can be diagonally disposed to each other, relative to a horizontal axis of the feedthrough assembly 415, thus resulting in a symmetrical staggered arrangement. In other embodiments, the feedthrough pins may be formed in a single or in multiple rows.

A feedthrough assembly 415 is structured and arranged as an interface between the control module connector 144 (see, FIG. 2) and the electronic sub-assembly 110 (see, FIG. 2) enclosed by the casing 414. The feedthrough assembly 415 along with the casing 414 hermetically seals the compartment that contains the electronic sub-assembly 110 and also electrically couples the electronic sub-assembly 110 with the connector contacts 314 (see, FIG. 3A) of the control module connector 144.

The feedthrough pins 440 and casing 414 can be made of any suitable material and may be the same or different materials. Examples of suitable materials include, but are not limited to, titanium, platinum, platinum-iridium, or any other suitable metal. (The term "metal" includes alloys unless indicated otherwise.) In at least some embodiments, the casing 414 is formed solely or primarily of metal. In at least some other embodiments, the casing 414 is not solely formed of a metal, but may also include one or more polymer or non-conductive portions and one or more metal portions. The region of the casing around the ceramic block 442, however, is typically a metal portion. The ceramic block 442 can be made of any suitable non-conductive ceramic material such as, for example, aluminum oxide, titanium dioxide, zirconia, and the like, or any suitable combination of ceramic materials. The metal braze 444 can be made using any suitable brazing material that will braze the feedthrough pins 440 and metal portion of the casing 414 to the ceramic block 442. For example, a gold braze can couple titanium, platinum, or platinum/iridium to a ceramic block of aluminum oxide.

A layer of glass material can be added to this feedthrough assembly. The layer of glass may provide one or more advantages such as, for example, enhance the hermetic seal; enhance electrical insulation between pins or between the pins and the casing; enhance adhesion of the materials of the assembly; reduce corrosion or reverse electroplating (e.g., "plating out"); or alloying the braze material with the solder; or any combination thereof.

Figures 5, 6:
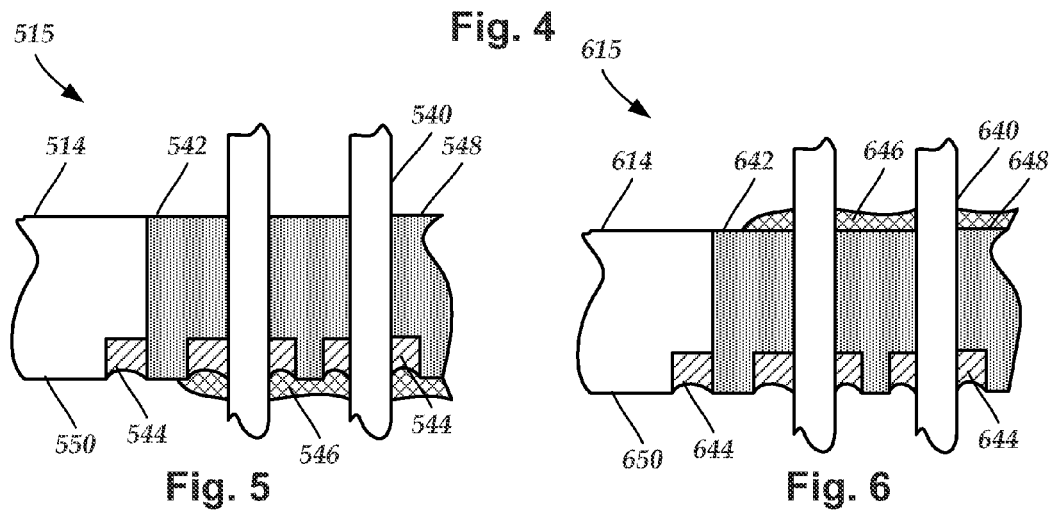
FIG. 5 is a schematic cross-sectional view of one embodiment of a feedthrough assembly and a portion of a casing of a control module, according to the invention.
FIG. 6 is a schematic cross-sectional view of a second embodiment of a feedthrough assembly and a portion of a casing of a control module, according to the invention.

FIG. 5 illustrates one embodiment of a feedthrough assembly 515 that includes a casing 514, feedthrough pins 540, ceramic block 542, metal braze 544, and glass layer 546. Side 548 is facing the header portion 112 (see, FIG. 2) and side 550 is facing the sealed compartment of the metal casing 514. In this embodiment, the glass layer 546 is disposed on side 550 facing the sealed compartment of the metal casing 514. The glass layer 546 is disposed on at least a portion of the ceramic block 542 and in contact with one or more of the feedthrough pins 540 (and is preferably in contact with each of the feedthrough pins 540) and preferably in contact with the portion of the metal braze disposed around the pins. In at least some embodiments, the glass layer may extend to cover a portion of the casing 514 or the portion of the metal braze 544 attaching the ceramic block 542 to the casing.

The glass layer 546 can be formed after the metal braze 544 is provided between the casing/pins and ceramic block. The glass layer 546 can be formed using any suitable technique including, but not limited to, firing glass-forming material to generate the glass layer. The forming process may be performed with one firing step or multiple firing steps with application of glass-forming material at each (or at least a subset) of the multiple firing steps. Because the glass layer 546 is formed after the metal braze 544, the firing temperature of the glass layer is preferably sufficiently low to prevent braze material melting or otherwise degrading the metal braze joint between the casing/pins and the ceramic block. In at least some embodiments, the firing temperature of the glass layer is at least 100° C., 200° C., or 300° C. less than the melting temperature of the metal braze.

Any suitable glass material can be used for the glass layer 546. The glass layer 546 is preferably biocompatible and does not include materials that may leach into the body with deleterious effect. In at least some embodiments, the glass layer 546 is formed of a non-silicate glass, such as, but not limited to, CABAL-12™.

The materials of the feedthrough assembly are selected so that the coefficients of thermal expansion (over the range of temperatures encountered during manufacture or during use) of the glass layer and one or more of the ceramic block, feedthrough pins, or casing are similar to reduce the risk of separation or cracking. In at least some embodiments, the glass layer 546 is formed of a material with a coefficient of thermal expansion that is no more than 25%, 20%, 15%, or 10% different from the coefficient of thermal expansion of the ceramic block, feedthrough pins, or casing or any combination of these elements over the range of temperatures expected during implantation and use of the control module (e.g., over the range of 20-40° C. or 25-40° C.) or during manufacture (e.g., in the range from 20° C. to the firing temperature of the glass layer).

When the glass layer 546 is formed over the metal braze 544, as illustrated in FIG. 5, the glass layer may reduce the risk of the material of the metal braze (e.g., gold) alloying with the solder used to attach the feedthrough pins to wires or the like for connecting the pins to the electronics subassembly. Such alloying of the metal braze with solder can degrade the braze joint by consuming or displacing the material of the metal braze. In addition, the glass layer 546 may augment a hermetic seal, improve pin-pin or pin-casing electrical isolation, avoid alloying with a solder, or any combination thereof.

FIG. 6 illustrates one embodiment of a feedthrough assembly 615 that includes a casing 614, feedthrough pins 640, ceramic block 642, metal braze 644, and glass layer 646. Side 648 is directed toward the header portion 112 (see, FIG. 2) and side 650 is within the sealed compartment of the metal casing 614. In this embodiment, the glass layer 646 is disposed on side 648 facing the header portion 112 and opposite the side 650 where the metal braze 644 is disposed. The glass layer 646 is disposed on at least a portion of the ceramic block 642 and in contact with one or more of the feedthrough pins 640 (and is preferably in contact with each of the feedthrough pins 640). In at least some embodiments, the glass layer may extend to cover a portion of the casing 614.

With the glass layer 646 on the side 650 of the ceramic block 642 opposite the side 648 where the metal braze 644 is disposed, the glass layer may reduce the risk of the metal braze "plating out" or corroding with applied electrical currents. The glass layer may act as a seal to protect/electrically isolate the metal braze. In addition, the glass layer 646 may augment a hermetic seal, improve header adhesion, improve pin-pin or pin-casing electrical isolation, avoid reverse electroplating, reduce corrosion, or any combination thereof.

Figure 7:
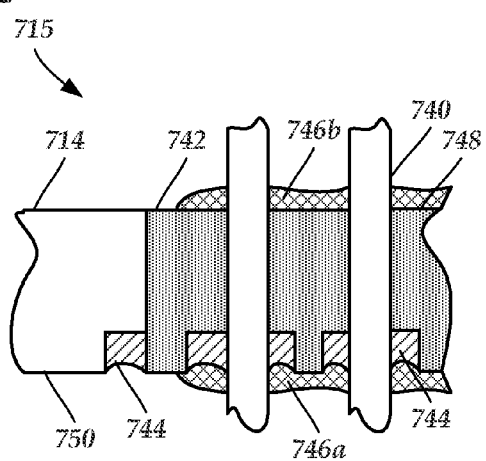
FIG. 7 is a schematic cross-sectional view of a third embodiment of a feedthrough assembly and a portion of a casing of a control module, according to the invention.

FIG. 7 illustrates one embodiment of a feedthrough assembly 715 that includes a casing 714, feedthrough pins 740, ceramic block 742, metal braze 744, and two glass layers 746a, 746b. Side 748 is directed toward the header portion 112 (see, FIG. 2) and side 750 is within the sealed compartment of the metal casing 714. In this embodiment, a glass layer 746a is disposed on side 750 of the ceramic block 742 facing the sealed compartment of the metal casing 714 and a glass layer 746b is disposed on side 748 facing the header portion. The glass layers 746a, 746b are disposed on at least a portion of the ceramic block 742 and in contact with one or more of the feedthrough pins 740 (and are preferably in contact with each of the feedthrough pins 740). In at least some embodiments, the glass layers 746a, 746b may extend to cover a portion of the casing 714 or the metal braze 744 attaching the ceramic block 742 to the casing.

Placing glass layers 746a, 746b on both sides of the ceramic block 742 can provide the benefits described above for the embodiments of both FIGS. 5 and 6 and provide two hermetic seals.

Any suitable methods or techniques can be used to form the feedback assemblies illustrated in FIGS. 5-7. The feedthrough pins are inserted through openings in the ceramic block. Typically, the metal braze between the pins and the ceramic block is formed before the glass layer as the brazing process is performed at a relatively high temperature, although in some embodiments, the metal braze and glass layer can be formed simultaneously in close sequential steps if the glass does not burn or degrade at the brazing temperature. The brazing of the ceramic block to the casing may occur simultaneously with, prior to, or after the brazing of the pins to the ceramic block.

The glass layer is formed after, or simultaneously with, brazing the pins to the ceramic block. The glass layer may be formed directly on top of the ceramic block or metal braze or both. In some embodiments, recesses may be provided in the ceramic block, feedthrough pins, or both to receive the glass layer. If glass layers are provided on both sides of the ceramic block (see, for example, FIG. 7), the glass layers may be formed simultaneously or sequentially.

The glass can be formed using any suitable method or technique and may be applied to the ceramic block using any suitable method. In at least some embodiments, a glass-forming material is placed in the desired region on the ceramic block. The glass-forming material may be provided in the form of, for example, a fluid, slurry, paste, powder, or the like. The glass-forming material is then fired to form the glass layer. The firing may include allowing the glass to flow to form a seal. In some embodiments, the formation of the glass layer may be a result of multiple applications of glass or glass-forming material with firing between at least some of the applications.

Figure 8:
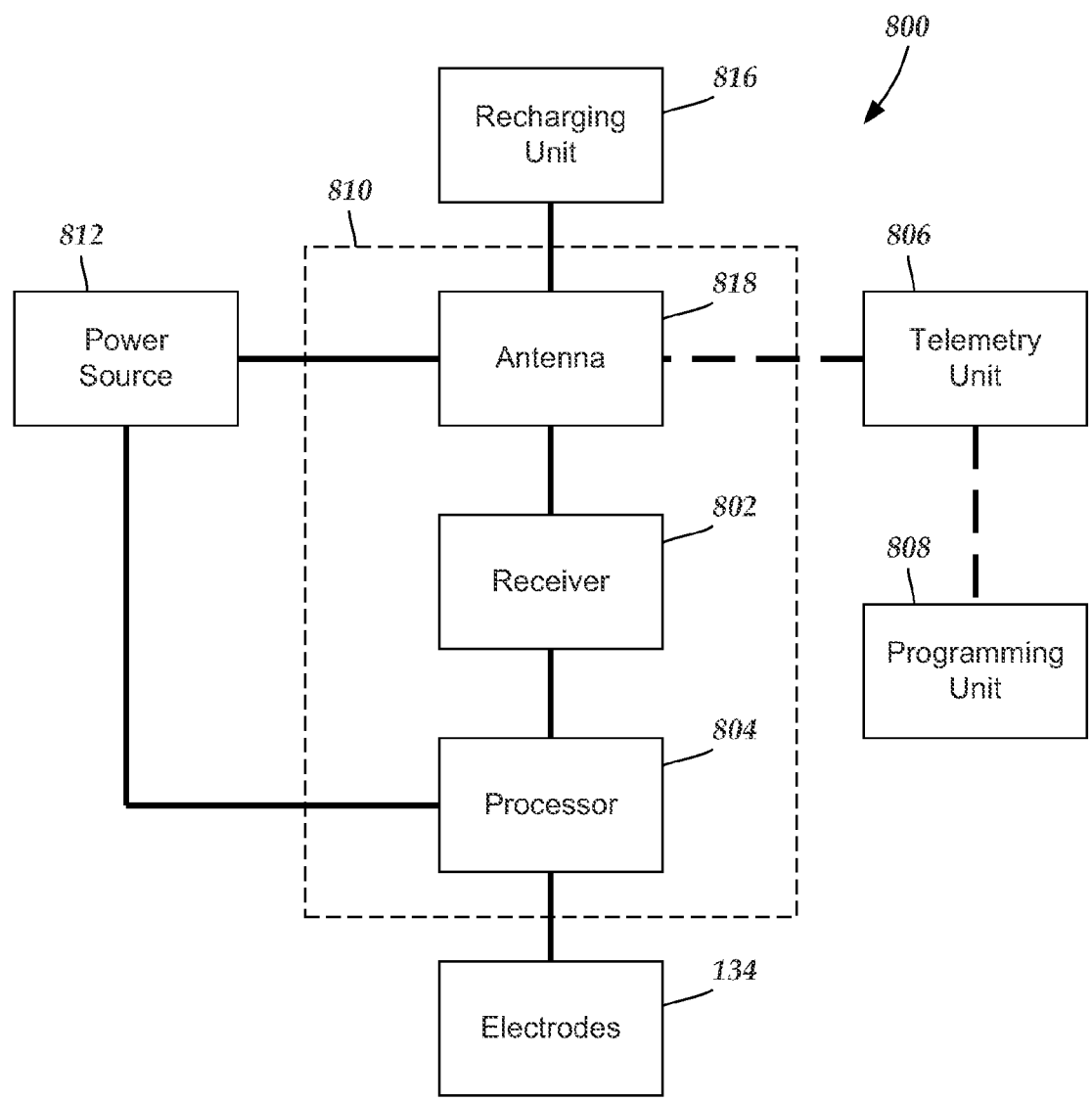
FIG. 8 is a schematic overview of an embodiment of components of a stimulation system, including an electronic subassembly disposed within a control module, according to the invention.

FIG. 8 is a functional block overview of one embodiment of components of an electrical stimulation system 800 including an electronic subassembly 810 disposed within a control module. It will be understood that the electrical stimulation system can include more, fewer, or different components and can have a variety of different configurations including those configurations disclosed in the stimulator references cited herein.

Some of the components (for example, power source 812, antenna 818, receiver 802, and processor 804) of the electrical stimulation system can be positioned on one or more circuit boards or similar carriers within a sealed housing of an implantable pulse generator, if desired. Any power source 812 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 8,437,193, incorporated herein by reference.

As another alternative, power can be supplied by an external power source through inductive coupling via the optional antenna 818 or a secondary antenna. The external power source can be in a device that is mounted on the skin of the user or in a unit that is provided near the user on a permanent or periodic basis.

If the power source 812 is a rechargeable battery, the battery may be recharged using the optional antenna 818, if desired. Power can be provided to the battery for recharging by inductively coupling the battery through the antenna to a recharging unit 816 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 804 is generally included to control the timing and electrical characteristics of the electrical stimulation system. For example, the processor 804 can, if desired, control one or more of the timing, frequency, strength, duration, and waveform of the pulses. In addition, the processor 804 can select which electrodes can be used to provide stimulation, if desired. In some embodiments, the processor 804 may select which electrode(s) are cathodes and which electrode(s) are anodes. In some embodiments, the processor 804 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 808 that, for example, allows modification of pulse characteristics. In the illustrated embodiment, the processor 804 is coupled to a receiver 802 which, in turn, is coupled to the optional antenna 818. This allows the processor 804 to receive instructions from an external source to, for example, direct the pulse characteristics and the selection of electrodes, if desired.

In one embodiment, the antenna 818 is capable of receiving signals (e.g., RF signals) from an external telemetry unit 806 which is programmed by a programming unit 808. The programming unit 808 can be external to, or part of, the telemetry unit 806. The telemetry unit 806 can be a device that is worn on the skin of the user or can be carried by the user and can have a form similar to a pager, cellular phone, or remote control, if desired. As another alternative, the telemetry unit 806 may not be worn or carried by the user but may only be available at a home station or at a clinician's office. The programming unit 808 can be any unit that can provide information to the telemetry unit 806 for transmission to the electrical stimulation system 800. The programming unit 808 can be part of the telemetry unit 806 or can provide signals or information to the telemetry unit 806 via a wireless or wired connection. One example of a suitable programming unit is a computer operated by the user or clinician to send signals to the telemetry unit 806.

The signals sent to the processor 804 via the antenna 818 and receiver 802 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 800 to cease operation, to start operation, to start charging the battery, or to stop charging the battery. In other embodiments, the stimulation system does not include an antenna 818 or receiver 802 and the processor 804 operates as programmed.

Optionally, the electrical stimulation system 800 may include a transmitter (not shown) coupled to the processor 804 and the antenna 818 for transmitting signals back to the telemetry unit 806 or another unit capable of receiving the signals. For example, the electrical stimulation system 800 may transmit signals indicating whether the electrical stimulation system 800 is operating properly or not or indicating when the battery needs to be charged or the level of charge remaining in the battery. The processor 804 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A control module for an electrical stimulation system, comprising:
    a casing defining a sealed inner compartment;
    an electronic subassembly disposed in the inner compartment of the casing;
    a header portion coupled to the casing and comprising a connector configured and arranged to receive a proximal end of at least one lead or lead extension, the connector comprising a plurality of conductive contacts configured and arranged to electrically couple to terminal contacts on the at least one lead or lead extension;
    a feedthrough assembly coupling the casing to the header portion and, in combination with the casing, sealing the inner compartment of the casing, the feedthrough assembly comprising
        a non-conductive ceramic block coupled to the casing,
        a plurality of conductive feedthrough pins passing through the ceramic block, the feedthrough pins electrically coupling the conductive contacts of the connector to the electronic subassembly disposed in the inner compartment of the casing,
        a metal braze coupling the feedthrough pins to the ceramic block, and
        a glass layer disposed on at least a portion of the ceramic block and in contact with at least one of the feedthrough pins.

2. The control module of claim 1, wherein the glass layer is directly disposed on at least a portion of the metal braze.

3. The control module of claim 1, wherein the ceramic block has a first side and a second side opposite the first side, wherein the metal braze is disposed on the first side of the ceramic block and the glass layer is disposed on the second side of the ceramic block.

4. The control module of claim 3, wherein the first side of the ceramic block faces the inner compartment of the casing.

5. The control module of claim 1, wherein the ceramic block has a first side and a second side opposite the first side, wherein the metal braze and the glass layer are both disposed on the first side of the ceramic block.

6. The control module of claim 5, further comprising a second glass layer disposed on the second side of the ceramic block and in contact with at least one of the feedthrough pins.

7. The control module of claim 1, wherein the feedthrough assembly, the casing, the metal braze, and the glass layer hermetically seal the inner compartment of the casing.

8. The control module of claim 1, wherein the glass layer is formed of a non-silicate glass.

9. The control module of claim 1, wherein the metal braze comprises gold.

10. An electrical stimulation system, comprising
    the control module of claim 1; and
    a lead having a proximal end configured and arranged to be received in the connector of the control module.

11. A control module for an electrical stimulation system, comprising:
    a casing defining a sealed inner compartment and comprising a metal portion;
    an electronic subassembly disposed in the inner compartment of the casing;
    a header portion coupled to the casing and comprising a connector configured and arranged to receive a proximal end of at least one lead or lead extension, the connector comprising a plurality of conductive contacts configured and arranged to electrically couple to terminal contacts on the at least one lead or lead extension;
    a feedthrough assembly between the casing and the header portion and, in combination with the casing, sealing the inner compartment of the casing, the feedthrough assembly comprising
        a non-conductive ceramic block coupled to the metal portion of the casing,
        a plurality of conductive feedthrough pins passing through the ceramic block, the feedthrough pins electrically coupling the conductive contacts of the connector to the electronic subassembly disposed in the inner compartment of the casing,
        a metal braze coupling the feedthrough pins to the ceramic block, and
        a glass layer disposed on at least a portion of the ceramic block and in contact with each of the feedthrough pins to form a hermetic seal around the feedthrough pins.

12. The control module of claim 11, wherein the ceramic block has a first side and a second side opposite the first side, wherein the metal braze is disposed on the first side of the ceramic block and the glass layer is disposed on the second side of the ceramic block.

13. The control module of claim 12, wherein the first side of the ceramic block faces the inner compartment of the casing.

14. The control module of claim 11, wherein the ceramic block has a first side and a second side opposite the first side, wherein the metal braze and the glass layer are both disposed on the first side of the ceramic block.

15. A method of forming a feedthrough assembly for a control module of an implantable electrical stimulation system, the method comprising:
    disposing a plurality of feedthrough pins through openings in a ceramic block;
    attaching the feedthrough pins to the ceramic block using a metal braze; and
    after attaching the feedthrough pins, forming a glass layer on at least a portion of the ceramic block and in contact with each of the feedthrough pins.

16. The method of claim 15, wherein forming a glass layer comprising forming the glass layer in contact with at least a portion of the metal braze.

17. The method of claim 15, wherein forming a glass layer comprises forming the glass layer on a first side of the ceramic block opposite a second side of the ceramic block where the metal braze is located.

18. The method of claim 17, further comprising forming a second glass layer on at least a portion of the second side of the ceramic block and in contact with each of the feedthrough pins and with the metal braze.

19. The method of claim 15, wherein forming a glass layer comprises firing a glass-forming material to form the glass layer at a temperature that is at least 100° C. less than a melting temperature of the metal braze.

20. The method of claim 15, wherein forming the glass layer comprises forming the glass layer through multiple applications of glass on the ceramic block.

\* \* \* \* \*